United States Patent [19]
Osypka

[11] Patent Number: 5,484,407
[45] Date of Patent: Jan. 16, 1996

[54] CATHETER WITH STEERABLE DISTAL END

[76] Inventor: Peter Osypka, Basler Strasse 109, D-7889 Grenzach-Wyhlen, Germany

[21] Appl. No.: 246,002

[22] Filed: May 19, 1994

[30] Foreign Application Priority Data

Jun. 24, 1993 [DE] Germany .............. 43 20 962.9

[51] Int. Cl.$^6$ .................. A61M 37/00; A61M 25/00
[52] U.S. Cl. .................. 604/95; 604/282; 128/657
[58] Field of Search .................. 604/43, 95, 264, 604/280, 282, 170; 128/656–658, 772

[56] References Cited

U.S. PATENT DOCUMENTS

| | | | |
|---|---|---|---|
| 2,688,329 | 9/1954 | Wallace | 604/95 |
| 4,033,331 | 7/1977 | Guss et al. | |
| 4,150,676 | 4/1979 | Jackson | |
| 4,456,017 | 6/1984 | Miles | 128/772 |
| 4,586,923 | 5/1986 | Gould et al. | 604/95 |
| 4,823,805 | 4/1989 | Wojcik | 128/736 |
| 4,906,230 | 3/1990 | Maloney et al. | 604/95 |
| 4,920,980 | 5/1990 | Jackowski | 128/786 |
| 5,030,204 | 7/1991 | Badger et al. | 604/95 |
| 5,041,085 | 8/1991 | Osborne et al. | 604/51 |
| 5,168,864 | 12/1992 | Shockey | 128/4 |
| 5,199,950 | 4/1993 | Schmitt et al. | 604/95 |
| 5,331,948 | 7/1994 | Utsumi et al. | 128/4 |
| 5,364,352 | 11/1994 | Cimino et al. | 604/95 |
| 5,368,564 | 11/1994 | Savage | 604/95 |
| 5,391,146 | 2/1995 | That et al. | 604/95 |
| 5,399,164 | 3/1995 | Snoke et al. | 604/95 |

FOREIGN PATENT DOCUMENTS

| | | |
|---|---|---|
| 0543539 | 5/1993 | European Pat. Off. . |
| 3819372 | 4/1990 | Germany . |
| 3920707 | 10/1991 | Germany . |
| WO92/14506 | 9/1992 | WIPO . |

OTHER PUBLICATIONS

The Random House College Dictionary: Revised Edition (Random House, Inc., 1979), p. 1065.

*Primary Examiner*—C. Fred Rosenbaum
*Assistant Examiner*—Adam J. Cermak

[57] ABSTRACT

A catheter for introduction into blood vessels or other passages in a patient's body has an elongated flexible tubular member with a readily flexible distal end portion, a less flexible intermediate portion and a proximal end portion. The distal end portion can be bent relative to the intermediate portion by a wire-, filament- or strip-shaped flexing element which extends through a lumen of the intermediate portion and through an extension of such lumen in the distal end portion and has a distal end affixed to the tip of the distal end portion. The intermediate portion is made stiffer than the distal end portion of the tubular member by appropriate shaping of the cross-sectional area of the intermediate portion and/or by resorting to one or more stiffening elements, such as a sleeve-like guide surrounding the flexing element in the respective lumen of the intermediate portion of the tubular member. The proximal end of the flexing element can be pulled, to thereby flex the distal end portion relative to the intermediate portion of the tubular member, by a rotary or reciprocable manipulator at the proximal end of the tubular member.

34 Claims, 5 Drawing Sheets

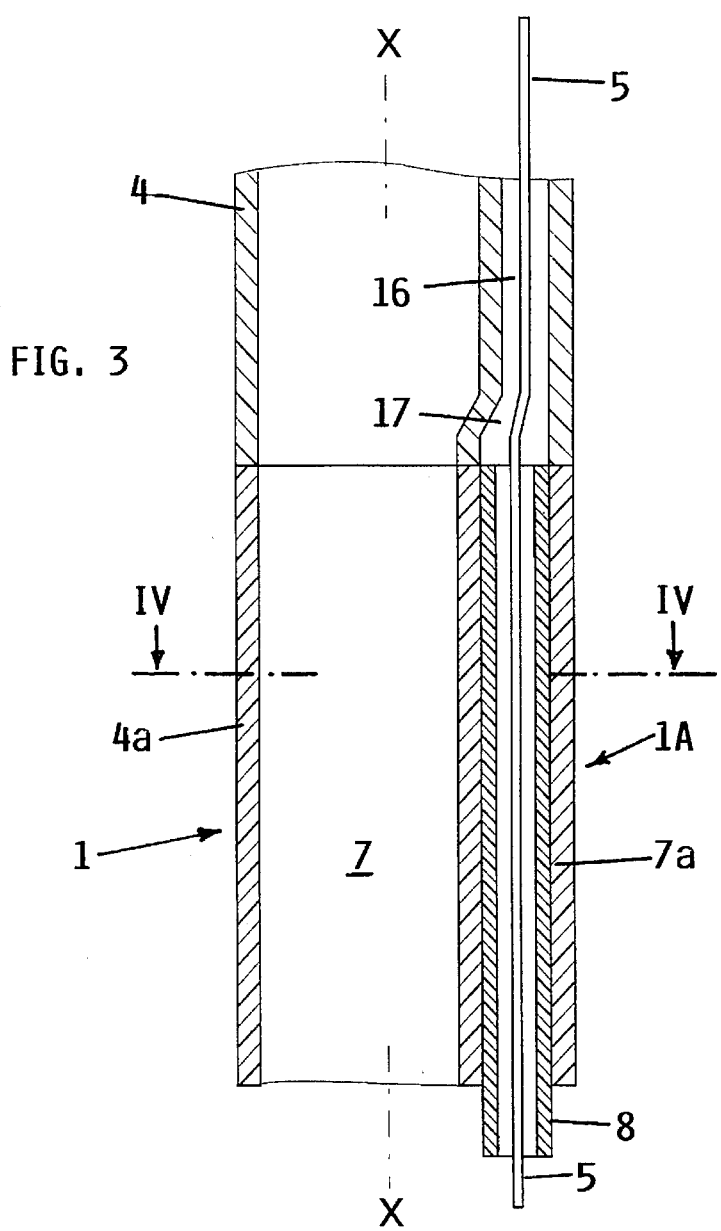
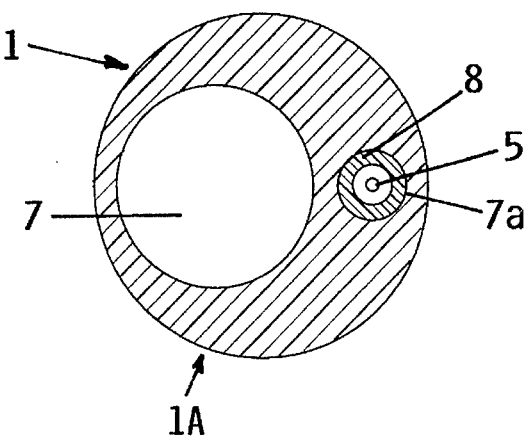

CATHETER WITH STEERABLE DISTAL END

BACKGROUND OF THE INVENTION

The invention relates to catheters in general, and more particularly to improvements in catheters of the type employing an elongated flexible tubular member and means for deforming (particularly flexing) the distal end of the tubular member so that such distal end can be steered into selected passages in a human body or another animal body, e.g., into progressively narrower blood vessels.

It is well known to make an elongated flexible tubular member of a catheter from a suitable plastic material and to provide the tubular member with at least one longitudinally extending passageway or lumen. It is also known to make such tubular members of materials having different rigidities. The flexibility of the tubular member of a catheter depends upon its intended use. As a rule, the tubular members of presently known and utilized catheters can be classified as relatively stiff, highly flexible or reasonably or relatively flexible (i.e., neither stiff nor highly flexible). As a rule, the ability of a tubular member to resist torsional stresses is more satisfactory if its stiffness is high whereas a highly flexible member offers much less resistance to such stresses. At least some resistance to torsional stresses is often necessary because a suitably configurated and dimensioned distal end can be caused to change its orientation in response to turning of the proximal end of the tubular member about its longitudinal axis in order to properly position the tip of the distal end for advancement into a selected blood vessel or another passage in a patient's body.

In accordance with another known proposal, the introduction of the flexible tubular member of a catheter into a selected portion of a body passage is preceded by the introduction of an elongated wire or an analogous guide member which extends through and beyond the distal end of the tubular member. The latter is then advanced along the already introduced guide until its distal end reaches the selected portion of the passage. An advantage of such catheters is that they can utilize highly flexible tubular members.

The aforediscussed conventional catheters exhibit the drawback that their versatility is not entirely satisfactory. For example, it is often necessary to employ a catheter having a highly or at least reasonably flexible tubular member with a distal end whose orientation can be changed in response to rotation of the tubular body about its longitudinal axis and which is readily flexible so that its tip can enter any one of a number of relatively narrow passages in the body of a patient. Not only the orientation but also the inclination of the tip of the distal end of the tubular member should be changed by a person having access to the proximal end of the catheter. The tip of the tubular member of a catheter which exhibits the just discussed advantages can be manipulated to penetrate first into a relatively large blood vessel, thereupon into a narrower vessel and finally into a very narrow or very small blood vessel. Such catheters would exhibit the desirable characteristics as concerns their ability to penetrate into narrow or even extremely narrow body passages, e.g., to scan an internal organ (such as a human heart), to make endoscopic images of internal organs with assistance from light conductors, to subject internal organs to a treatment with one or more laser beams and/or for other purposes. Furthermore, one or more lumina of a properly inserted tubular member can serve for convenient and rapid introduction of various instruments (such as, for example, biopsy tongs) as well as for introduction of flowable pharmaceutic products, medications and/or others. Moreover, certain treatments can involve the introduction of probes which carry electrodes, e.g., in order to determine the electrical potential at the heart of a patient or to perform a high-frequency ablation. Still further, one or more lumina of a properly inserted tubular member forming part of a catheter can be utilized to permit convenient evacuation of liquids, contaminants and/or other flowable substances as well as to permit the introduction of diagnostic, surgical and/or therapeutic instruments.

German Pat. No. 39 20 707 A1 discloses a catheter with an elongated flexible tubular member having a distal end whose curvature can be altered by an eccentrically mounted pull wire. The tubular member of the patented catheter is provided with an external reinforcement or bead having a longitudinally extending passage for the pull wire. The distal end of the pull wire extends from the passage of the bead and is connected to the tip of the distal end of the tubular member so that the inclination of the distal end of the tubular member can be altered in response to the application of a pull to the proximal end of the wire. A drawback of the patented catheter is that the exposed portion of the pull wire between the distal end of the passage in the bead and the tip of the distal end of the tubular member is likely to damage the tissue in the body of a patient, e.g., in a human heart and particularly in a ventricle of the heart. Thus, a heart valve (such as a mitral valve) is likely to be damaged by the exposed portion of the pull wire if the distal end of the tubular member forming part of the patented catheter is to advance through the septum and into the the left atrium, thence through the mitral valve and into the left ventricle of a patient.

Another drawback of the patented catheter is that the provision of a tubular bead at the exterior of the tubular member of the catheter contributes to the cost and reduces the flexibility of a large part of the tubular member. At the very least, the external bead causes the tubular member to exihibit different flexibilities in different directions. Furthermore, if the tubular member is or should be quite flexible, the exertion of a pull upon the proximal end of the wire is likely to cause undesirable flexing of the entire tubular member rather than a desired flexing of the distal end of the tubular member. Thus, there exists an urgent need for catheters whose distal ends can be readily introduced into selected passages of a patient's body without causing irritation, damage or undesirable flexing.

OBJECTS OF THE INVENTION

An object of the invention is to provide a catheter which exhibits all advantages but not the disadvantages of the aforediscussed conventional catheters.

Another object of the invention is to provide a simple and inexpensive but highly versatile catheter which is not likely to irritate or damage the tissue in a patient's body.

A further object of the invention is to provide a catheter which is constructed and assembled in such a way that only a selected portion of its tubular member can be flexed in response to manipulation of a flexing element at the proximal end of the tubular member.

An additional object of the invention is to provide a catheter whose tubular member need not be provided with an external bead for confinement of a pull wire or the like.

Still another object of the invention is to provide a novel and improved flexible tubular member for use in the above outlined catheter.

A further object of the invention is to provide a novel and improved one-piece tubular member for use in the above outlined catheter.

Another object of the invention is to provide a novel and improved composite tubular member for use in the above outlined catheter.

An additional object of the invention is to provide a novel and improved combination of a tubular member and a flexing element for use in the above outlined catheter.

Still another object of the invention is to provide a novel and improved method of manipulating a flexible catheter.

A further object of the invention is to provide a novel and improved method of manipulating the above outlined novel catheter.

SUMMARY OF THE INVENTION

The invention is embodied in a catheter comprising an elongated tubular member including a distal end portion having a first flexibility, an elongated intermediate portion having a lesser second flexibility and at least one longitudinally extending lumen. The tubular member has an at least substantially circular (including truly circular, oval and elliptical) cross-sectional outline, and the catheter further comprises means for deforming the distal end portion of the tubular member. The deforming means includes an elongated flexible element which extends within the cross-sectional outline of the tubular member from the distal end portion, through the intermediate portion and to a proximal end portion of the tubular member. The flexing element is moved relative to and longitudinally of the intermediate portion to thereby change the inclination of the distal end portion relative to the intermediate portion. The improved catheter further comprises a guide for the flexing element, and such guide is also disposed within the at least substantially circular outer cross-sectional outline of the tubular member.

At least a major portion of the flexing element is preferably spaced apart from and substantially parallel to the central longitudinal axis of the tubular member. The latter can contain or can consist of a suitable plastic material.

The distal end portion of the tubular member and at least that part of the intermediate portion which is adjacent the distal end portion are preferably devoid of any, or of any pronounced, external protuberances in the form of longitudinally extending beads and/or others. Furthermore, the distal end portion of the tubular member and at least that part of the intermediate portion which is adjacent the distal end portion are preferably provided with at least substantially smooth external surfaces.

The flexibility of the elongated intermediate portion relative to the flexibility of the distal end portion of the tubular member is or can be reduced by reducing means within the cross-sectional outline of the tubular member. The means for reducing the flexibility of the intermediate portion can constitute or include the aforementioned guide for the flexing element. Such means for reducing can include at least one elongated sleeve which surrounds the flexing element. The sleeve can contain or it can consist of a suitable metallic or plastic material. The distal end of the flexing element is preferably disposed within the distal end portion of the tubular member and preferably extends or can extend beyond the sleeve. For example, the distal end of the sleeve can be disposed at least close to the distal end of the intermediate portion of the tubular member. Furthermore, the distal portion or end of the flexing element can be affixed to that distal (free) end of the distal end portion which is remote from the intermediate portion of the tubular member. The distal portion of the flexing element can extend longitudinally of the distal end portion and within the aforementioned outline of the tubular member.

The inner diameter of the aforementioned sleeve or guide for the flexing element can be within the range of between approximately 0.2 and 0.8 mm, and the outer diameter of such sleeve can be within the range of between approximately 0.33 and 1 mm. The flexing element can be received within its sleeve with a radial clearance of between approximately 0.01 and 0.1 mm.

The flexing element can constitute at least one length of wire, thread or band, and the sleeve can be made of high-quality steel, e.g., stainless steel.

Instead of consisting of or including one or more sleeves, the aforementioned guide for the flexing element can include a first section of the tubular member which has a greater wall thickness than another section of the tubular member. The first section can extend longitudinally of the intermediate portion of the tubular member and can be provided with one or more longitudinally extending lumina for one or more flexing elements. Such first section is adjacent to and can surround the flexing element and the other section can be disposed diametrically opposite the first section with reference to the longitudinal axis of the tubular member.

The means for reducing the flexibility of the intermediate portion of the tubular member, as compared with the flexibility of the distal end portion, can comprise an elongated stiffening element (e.g., a length of wire, a filament or a strip) which is disposed in the intermediate portion of the tubular member, preferably at least substantially diametrically opposite the flexing element. The distal end of the stiffening element is bonded or otherwise affixed to the intermediate portion of the tubular member at the distal end portion of such member. The intermediate portion of the tubular member can include a wall of substantially constant thickness, and such wall can be provided with a longitudinally extending first lumen for the flexing element and a longitudinally extending second lumen for the stiffening element. The first and second lumina of the tubular wall can be disposed at least substantially diametrically opposite each other. The tubular member can be provided with at least one additional lumen, e.g., for introduction of fluid medicaments or for introduction of one or more implements or instruments into a selected portion of a patient's body. Irrespective of the lumen for the flexing element and/or the lumen for the stiffening element, the tubular member can be provided with one or more lumina in addition to the at least one lumen.

It is further within the purview of the invention to provide the tubular member with the at least one lumen and with a second lumen for the flexing element. A portion (e.g., a metallic or plastic sleeve) of the guide means can be disposed in the second lumen. An extension of the second lumen can be provided in the distal end portion of the tubular member to receive the respective (distal) portion of the flexing element. The arrangement is preferably such that the distal portion of the flexing element in the extension of the second lumen is disposed at a lesser first distance and the portion of the flexing element in that portion of the second lumen which is provided in the intermediate portion of the tubular member is disposed at a greater second distance from the external surface of the tubular member.

The novel features which are considered as characteristic of the invention are set forth in particular in the appended claims. The improved catheter itself, however, both as to its construction and the method of assembling and utilizing the same, together with additional features and advantages thereof, will be best understood upon perusal of the following detailed description of certain presently preferred specific embodiments with reference to the accompanying drawings.

BRIEF DESCRIPTION OF THE DRAWINGS

FIG. 3 is an enlarged fragmentary central longitudinal sectional view of a detail within the phantom-line circle B in FIG. 1, showing a part of the distal end portion and the adjacent part of the intermediate portion of the flexible member as well as the flexing element and its sleeve within the outer cross-sectional outline of the tubular member;

FIG. 4 is a sectional view substantially as seen in the direction of arrows from the line IV—IV in FIG. 3;

DESCRIPTION OF PREFERRED EMBODIMENTS

Figures 1, 2:
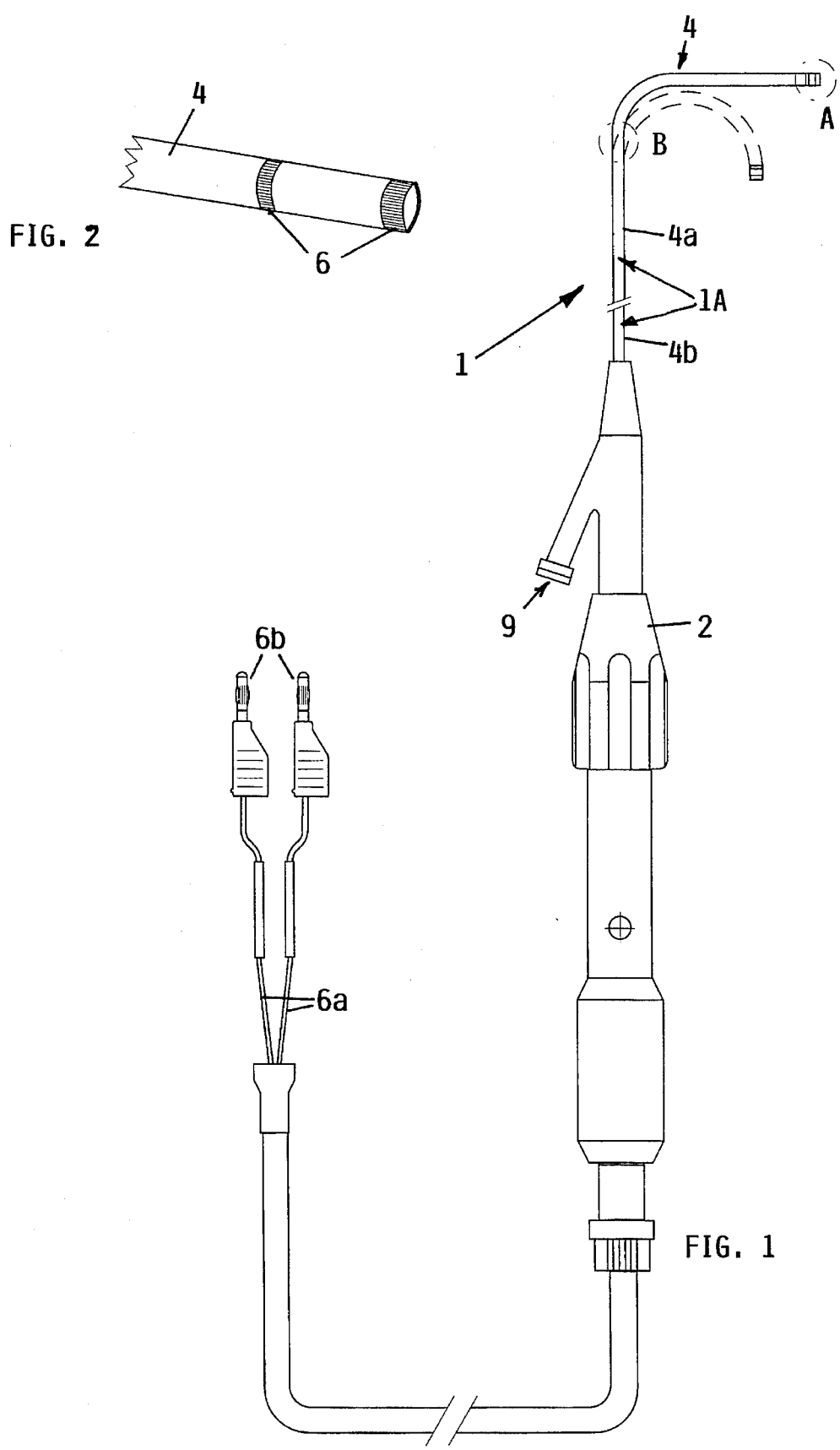
FIG. 1 is a fragmentary schematic elevational view of a catheter which embodies one form of the present invention, one position of the readily flexible distal end portion of the tubular member being shown by solid lines and a different position of the distal end portion being indicated by broken lines.
FIG. 2 is an enlarged perspective view of that part of the distal end portion of the tubular member which is disposed within the phantom-line circle A in FIG. 1.

FIGS. 1 to 4 illustrate those parts of a novel and improved adjustable or regulatable catheter 1 which are necessary for a complete understanding of the invention. The reference character 2 denotes a rotary manipulator knob which can be replaced with a reciprocable manipulator 3 (shown in FIG. 9). The purpose of the manipulator 2 is to change the inclination of the flexible distal end portion 4 of an elongated flexible tubular member 1A relative to an elongated intermediate portion 4a. The tubular member 1A further includes a proximal end portion 4b adjacent the intermediate portion 4a and carrying the manipulator 2. The means for deforming the distal end portion 4 relative to the adjacent part of the intermediate portion 4a includes an elongated flexing element 5, e.g., a length of wire, which is caused to move longitudinally of and relative to the intermediate portion 4a in response to rotation of the manipulator 2. The distal end portion 4 carries electrodes 6 (FIG. 2) which can be introduced into a patient's heart or into another internal organ in response to appropriate flexing of the end portion 4. The electrodes 6 can be connected to a suitable instrument (not shown) by way of conductors 6a extending from the proximal end portion 4b of the tubular member 1A and being provided with appropriate terminals 6b.

FIGS. 3 and 4 show that the tubular member 1A is provided with a longitudinally extending lumen 7 having a circular cross-sectional outline and having an axis which is spaced apart from and at least substantially parallel to the central longitudinal axis of the tubular member. In lieu of or in addition to the conductors 6a, the lumen 7 can also serve for introduction of therapeutic instruments, endoscopes or other parts which are to be introduced into a patient's body (e.g., into a human heart) with assistance from the improved catheter 1.

The flexing element 5 is also spaced apart from and is at least substantially parallel to the central longitudinal axis of the tubular member 1A. This enables the physician in charge to exert upon the element 5 a pull which is necessary to incline the free end or tip of the distal end portion 4 to an optimum position relative to the intermediate portion 4a. Such pull is exerted in response to rotation of the manipulator 2 or in response to axial displacement of the manipulator 3. When the tip of the distal end portion 4 assumes an optimum position relative to the adjacent part of the intermediate portion 4a, the entire tubular member 1A can be moved longitudinally in order to introduce the distal end portion 4 into a selected passage in the body of a patient.

The tubular member 1A which is shown in FIGS. 1 to 4 has a truly circular outer cross-sectional outline (see particularly FIG. 4). However, it is equally possible to employ a tubular member having a substantially circular (such as oval or elliptical) outer cross-sectional outline. In accordance with a feature of the present invention, at least the external surface of the distal end portion 4 and of that part of the intermediate portion 4a which is to be introduced into the body of a patient is at least substantially smooth and is also devoid of any appreciable or noticeable projections or protuberances which could affect the ability of the tubular member 1A to turn in an internal passage of a patient's body. The tubular member 1A is preferably made of a suitable flexible plastic material and, at least in the embodiment of FIGS. 1 to 4, the wire-like or thread-like flexing element 5 does not extend outwardly beyond the cross-sectional outline of the distal end portion 4 and/or that part of the intermediate portion 4a which is to penetrate into a patient's body.

The flexing element 5 is confined in and is movable longitudinally in a tubular sleeve-like guide 8 which has a distal end (see FIG. 3) at the junction of the distal end portion 4 and the intermediate portion 4a of the tubular member 1A. The flexibility of the distal end portion 4 is more pronounced than that of the intermediate portion 4a; this ensures that intentional flexing of the distal end portion 4 does not necessarily result or does not result in any, or any pronounced, flexing of the intermediate portion 4a. The flexibility of the intermediate portion 4a (as compared with the flexibility of the distal end portion 4) is reduced by the provision of the tubular sheath- or sleeve-like guide 8 as well as by appropriate shaping of the wall of the tubular member 1A. This wall has a relatively thin section remote from the sleeve-like guide 8 and a thicker section disposed diametrically opposite the relatively thin section and surrounding the guide 8 in the region of the intermediate portion 4a. The relatively thick section of the wall of the tubular member 1A between the distal end portion 4 and the manipulator ensures that the application of a pull to the flexing element 5 results in flexing of the distal end portion 4 but in much less pronounced flexing or no flexing at all of the intermediate portion 4a. The difference between the flexibilities of the distal end portion 4 and intermediate portion 4a of the tubular member 1A is particularly pronounced if this member is made of a relatively soft elastomeric plastic material, if the difference between the thicknesses of the two sections of the wall of the member 1A is rather pronounced and/or if the sleeve 8 offers a relatively strong resistance to deformation of the intermediate portion 4a. Nevertheless, at least that part of the intermediate portion 4a which is expected to enter a body cavity (e.g., a large blood vessel) is sufficiently flexible to ensure that it can follow the path which is defined by the body cavity and which need not be and often is not a straight path.

The sleeve 8 can be made of a metallic material or a relatively hard plastic material. As already mentioned above, and as shown in FIG. 3, the distal end of the sleeve 8 can be located at the boundary between the intermediate portion 4a and the distal end portion 4 of the tubular member 1A. The distal end of the flexing element 5 extends beyond the distal end of the sleeve 8 but remains within the outline of the tubular member 1A. The tip or free end of the element 5 is suitably secured to the tip or free end of the distal end portion 4 of the tubular member 1A. If the person in charge actuates the manipulator 2 in a sense to exert a pull upon the flexing element 5, the latter flexes (either primarily or exclusively) the distal end portion 4, e.g., from the position which is shown in FIG. 1 by solid lines to the position which is shown in FIG. 1 by broken lines, so that the tip of the distal end portion 4 is free to leave a relatively large passage and to enter a narrower passage. The angular position of the distal end portion 4 about the central longitudinal axis of the intermediate portion 4a can be altered by rotating the proximal end portion 4b about such axis.

FIG. 1 shows that the manipulator 2 is provided with an inlet 9 which opens into the large-diameter lumen 7 of the tubular member 1A. The inlet 9 can serve for introduction of one or more catheters, electrodes, endoscopes or other mechanical parts and/or of medicaments and/or other flowable substances.

The sleeve-like tubular guide 8 can have a relatively small outer diameter, e.g., in the range of between approximately 0.33 or 0.4 mm and 1 mm, and the inner diameter of this guide can be in the range of between approximately 0.2 mm and 0.8 mm. In other words, the wall thickness of the sleeve-like guide 8 need not appreciably exceed 0.1 mm. Nevertheless, even a relatively thin-walled guide can contribute rather significantly to increased stiffness (i.e., less pronounced flexibility) of the intermediate portion 4a of the tubular member 1A. At the same time, the intermediate portion 4a still remains sufficiently flexible to ensure that it can follow a path which is defined by a blood vessel or another internal passage in the body of a patient even if such path includes arcuate portions or otherwise departs from a straight path.

The diameter or cross-sectional area of the flexing element 5 can be selected in such a way that it is received in the lumen of the sleeve-like guide 8 with a relatively small clearance, e.g., a clearance in the range of between approximately 0.01 mm and 0.1 mm. Such clearance suffices to ensure that the flexing element 5 will offer little resistance to axial movement longitudinally of and relative to the intermediate portion 4a in order to change the inclination of the distal end portion 4 of the tubular member 1A. The material of the tubular member 1A is preferably such that the distal end portion 4 exhibits at least some tendency, or even a rather pronounced tendency, to reassume a predetermined starting position of inclination relative to the adjacent part of the intermediate portion 4a. A presently preferred material for the guide 8 is a relatively hard but still somewhat flexible plastic material or a stainless steel or another metal which can stand the corrosive influence of body fluids and medicaments or other fluids which are to be introduced into the body of a patient. The utilization of a strongly corrosion-resistant material for the guide 8 is desirable and advantageous even if this guide is tightly embedded into the smaller-diameter lumen 7a in the relatively thick section of the wall of the tubular member 1A. The presently preferred material for the flexing element 5 is a metallic substance which can be used regardless of whether the element 5 is a wire, a filament or a strip. An advantage of a small-diameter wire or filament or of a relatively thin strip is that the dimensions of the guide 8 can be reduced accordingly, i..e, the guide 8 and the flexing element 5 therein occupy a minimal amount of space within the circular or at least substantially circular outline of the tubular member 1A.

The illustrated larger-diameter lumen 7 of the tubular member 1A is eccentric with reference to the central longitudinal axis of the intermediate portion 4a (see particularly FIGS. 3 and 4). However, if the space requirements of the sleeve-like guide 8 and the flexing element 5 therein are minimal, the illustrated member 1A can be replaced with a member having a concentric lumen 7. It is also possible to provide the tubular member 1A or an equivalent tubular member with a lumen which, in contrast to the lumen 7, has an oval, elliptical or other selected cross-sectional outline departing from a truly circular outline.

FIG. 3 shows that the lumen 7a of the intermediate portion 4a includes an extension 16 which is provided in the adjacent portion of the wall of the distal end portion 4. The extension 16 of the lumen 7a is provided in a relatively thick longitudinally extending section of the wall of the distal end portion 4. The absence of an extension of the sleeve 8 into the portion 16 of the lumen 7a is desirable because this also contributes to the establishment of a rather pronounced difference between the flexibilities of the distal end portion 4 and the intermediate portion 4a. The reference character 17 denotes in FIG. 3 a gradual transition between the surface bounding the lumen 7a in the intermediate portion 4a and the surface bounding the extension 16 in the distal end portion 4. The slope of the transition 17 is such that the distal end portion of the flexing element 5 is nearer to the external surface of the right-hand section of the wall of the distal end portion 4 than to the external surface of the right-hand section of the wall of the intermediate portion 4a (all as viewed in FIG. 3). Such guidance of the flexing element 5 contributes to the ability of the distal end of the element 5 to flex the end portion 4 relative to the portion 4a in response to the application of a pull which urges the distal end of the element 5 to move nearer to the manipulator. Otherwise stated, the placing of the distal end of the flexing element 5 close to the external surface of the thicker section of the distal end portion 4 lengthens the lever arm of the portion 4 and ensures highly predictable flexing of the tubular member 1A in the region of the transition 17, i.e., at the boundary between the distal end portion 4 and the intermediate portion 4a.

The central longitudinal axis of the tubular member 1A is shown at X—X (see FIG. 3). The distance of the wire-like or thread-like or filament-like flexing element 5 from the axis X—X in the distal end portion 4 is the same or nearly the same as the distance of the axis X—X from the right-hand side of the external surface of the sleeve-like guide 8 in the intermediate portion 4a of the tubular member 1A. Otherwise stated, that portion of the element 5 which is adjacent the transition 17 is flexed away from the axis X—X. This, too, renders it possible to flex the end portion 4 in a highly predictable manner in response to the actuation of the manipulator 2.

An important advantage of the improved catheter 1 is that the flexing element 5 does not and need not extend outwardly beyond the external surface of the distal end portion 4 and/or the intermediate portion 4a, i.e., the element 5 need not extend outwardly beyond the outline of the cross-sectional area of that part of the tubular member 1A which is likely to enter the body of a patient. This prevents the flexing element 5 from damaging the tissue around the distal end portion 4 and/or around the intermediate portion 4a without affecting the ability of the element 5 to flex the distal end portion 4 to a desired extent. The feature that the distal end portion 4 can be flexed to a desired extent is important and desirable, especially when the catheter 1 is to be introduced into relatively narrow blood vessels or other passages in the body of a patient.

Another advantage of the improved catheter is that the flexibility of the distal end portion 4 exceeds the flexibility of the intermediate portion 4a. This contributes to the aforediscussed ability of the portion 4 to flex to a desired extent relative to the portion 4a while the shape of the portion 4a remains unchanged even though the portion 4a is capable of readily following the outline of the passage in which the portion 4a is received at the time a physician actuates the manipulator 2 in order to enable the tip of the distal end portion 4 to enter a selected passage which is or which may be narrower than the passage receiving the intermediate portion 4a. It has been found that the distal end portion 4 can be flexed relative to the intermediate portion 4a through an angle of up to, or even in excess of, 180° which greatly enhances the versatility of the catheter 1.

A further advantage of the improved catheter 1 is that it can operate properly without the provision of a bead corresponding to the external bead disclosed in the aforediscussed German Pat. No. 39 20 707 A1. This ensures that the external surfaces of the distal end portion 4 and at least the adjacent part of the intermediate portion 4a are devoid of any external projections or protuberances which would be likely to interfere with proper manipulation of an inserted catheter, e.g., by offering excessive resistance to rotation of the distal end portion and/or the intermediate portion of the tubular member. The external surfaces of the portions 4 and 4a are preferably smooth. It can be said that the improved catheter 1 exhibits all advantages but avoids the drawbacks of the catheter which is disclosed in the German patent. As actually shown, the improved tubular member 1A is provided with an internal "bead"(namely the relatively thick right-hand section of the wall of the tubular member 1A shown in FIGS. 3 and 4) so that such "bead" does not interfere with the ability of the distal end portion 4 to flex relative to the intermediate portion 4a and/or with the ability of the portions 4, 4a to turn about the axis X—X of the tubular member 1A.

Still another important advantage of the improved catheter 1 is that the flexing element 5 and its guide 8 do not take up a substantial amount of space within the outline of the cross-sectional area of the tubular member 1A. In addition, the element 5 and its guide 8 contribute to the establishment of the desirable difference between the flexibilities of the portions 4 and 4a of the tubular member 1A. The establishment of such difference is further facilitated by the aforediscussed shaping of the tubular wall of the member 1A, i.e., that the right-hand section (as viewed in FIG. 3 or 4) of such wall is thicker than the left-hand section which is disposed at least substantially diametrically opposite the thicker section.

The length of the distal end portion 4 can be a small or a very small fraction of the length of the intermediate portion 4a.

The provision of the aforediscussed sleeve-like guide 8 in the intermediate portion 4a to perform the dual function of guiding the longitudinally movable flexing element 5 and of simultaneously enhancing the ability of the intermediate portion 4a to resist undesirable or excessive flexing is believed to constitute an independent innovation which is of patentable significance and can be utilized in combination with the improved catheter 1 as well as in combination with the flexible tubular members of conventional catheters. If desired, the guide 8 could include a readily flexible extension in the extension 16 of the lumen 7a; however, the absence of such extension of the guide 8 in the portion 4 is preferred at this time because this further enhances the ability of the portion 4 to be readily and predictably bent relative to the portion 4a.

Since the inner and the outer diameters of the sleeve-like guide 8 are very small, the installation of such guide within the outline of the tubular member 1A does not present any serious problems, i.e., the outer diameter of the member 1A is not or need not be appreciably increased for the purpose of providing room for the guide 8 and the flexing element 5 within the outline of the external surface of such tubular member. As already explained hereinbefore, the outer diameter of the guide 8 need not exceed and can be a mere fraction of 1 mm.

If the flexing element 5 is an elongated strip, the guide 8 can be flattened (see FIG. 8) so that the parts 5 and 8 then take up even less room than the parts 5, 8 of FIGS. 3 and 4 (as seen in the radial direction of the tubular member 1A). The cross section of a strip-shaped flexing element (such as can be received in the guide 8 of FIG. 8) preferably extends in the circumferential direction of the respective tubular member.

Though the sleeve-like guide 8 of the catheter 1 which is shown in FIGS. 1 to 4 is embedded in the relatively thick section of the tubular wall of the member 1A, it is also possible to only partially embed the guide 8 into the material of the member 1A or to have such guide or an equivalent guide installed in the lumen 7. This renders it possible to employ a tubular member having a constant wall thickness and to enhance the resistance of the intermediate portion 4a to excessive flexing solely by the corresponding portions of the guide 8 and flexing element 5 and/or in another suitable manner. Still further, it is even possible to omit the guide 8 altogether and to rely only upon the thicker section of the tubular wall of the member 1A to ensure that the flexibility of the distal end portion exceeds the flexibility of the intermediate portion 4a. The provision of a discrete lumen 7a for the guide 8 and the flexing element 5 therein is preferred at this time because this leaves more room for introduction of instruments and/or medicaments through the lumen 7. Furthermore, the guide 8 and/or the element 5 cannot come in contact with instruments and/or medicaments. It is also possible to rely solely on the thicker section of the wall of the member 1A in order to ensure that the flexibility of the distal end portion 4 will exceed that of the intermediate portion 4a and to have the element 5 extend first through the lumen 7 within the intermediate portion 4a and thereupon through the lumen 16 in the distal end portion 4.

The catheter 1 of FIGS. 1 to 4 exhibits the additional advantage that the ability of the element 5 to flex the distal end portion 4 relative to the intermediate portion 4a is enhanced by causing the element 5 to move radially of and away from the axis X—X in the transition zone 17 between the main portion of the lumen 7a in the portion 4a and the extension 16 of such lumen in the end portion 4. This places the element 5 in the end portion 4 as close to the external surface of the tubular member 1A as the rightmost portion of the guide 8 (refer again to FIGS. 3 and 4).

The provision of the extension 16 in the distal end portion 4 of the tubular member 1A is often desirable and advantageous because it reduces the resistance of the end portion 4 to bending under the action of the flexing element 5. The provision of the lumen 7a in the wall of the intermediate portion 4a does not unduly reduce the resistance to flexing of the portion 4a by the element 5 because the lumen 7a is provided in the relatively thick section of the wall of the member 1A and also because the lumen 7a receives the guide 8 whose stiffening action can be selected in a manner to ensure that the portion 4a can exhibit a desired and optimal resistance to undue flexing.

The placing of the flexing element 5 or an equivalent flexing element close to the external surface of the tubular member 1A is particularly important within the distal end portion 4 and especially if the sleeve-like guide 8 is omitted. Such placing or positioning of the element 5 in the distal end portion 4 invariably ensures or is more likely to ensure predictable bending of the end portion 4 relative to the intermediate portion 4a in response to the application of pull to the proximal end of the element 5, even if the guide 8 is omitted. It has been found that, even in the absence of the guide 8, the flexing element 5 can be manipulated to bend the distal end portion 4 through an angle of at least up to 180°. This is amply sufficient to ensure that the improved catheter can be introduced into large, medium large and very narrow blood vessels or other passages in the body of a patient. All that counts is to ensure that the flexibility of the distal end portion 4 exceeds the flexibility of the intermediate portion 4a and that the means for bending the distal end portion 4 be confined within the preferably at least substantially circular cross-sectional outline of the tubular member 1A.

The catheter 1 of FIGS. 1 to 4 can be utilized with particular advantage for introduction of its distal end portion 4 into the heart of a patient. The electrodes 6 then serve to transmit intracardial signals for evaluation by the physician in charge.

Figure 5:
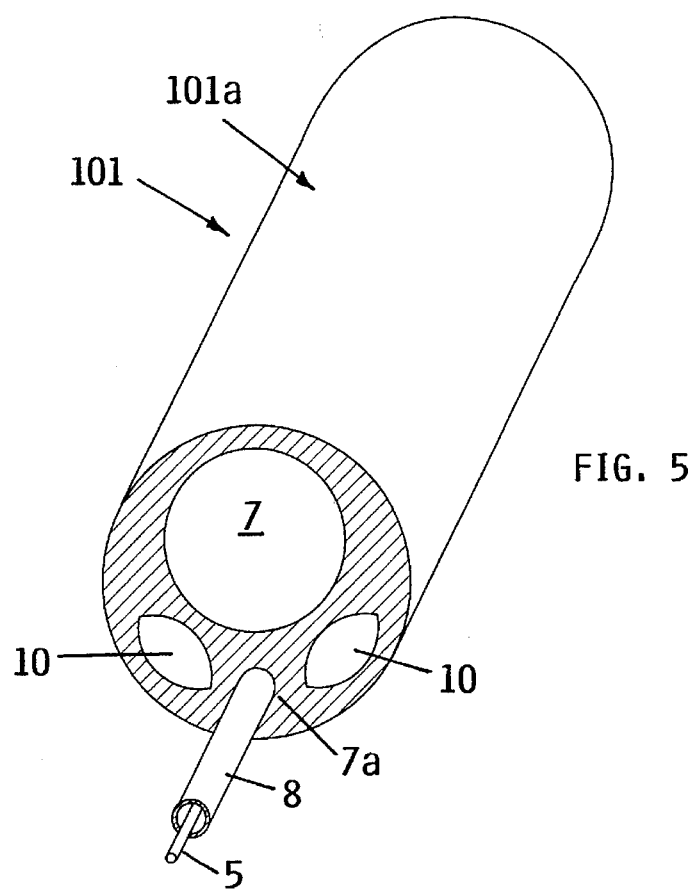
FIG. 5 is a greatly enlarged fragmentary partly perspective and partly cross-sectional view of a catheter constituting a first modification of the catheter which is shown in FIGS. 1 to 4.

FIG. 5 shows a portion of a modified catheter 101. The difference between the tubular member 101A of the catheter 101 and the tubular member 1A of the catheter 1 is that the tubular member 101A is provided with two additional lumina 10 which flank the lumen 7a for the guide 8 and the flexing element 5. Thus, the lumina 10 are also provided in the relatively thick section of the tubular member 101A. The additional lumina 10 can serve for controlled introduction of electrodes, thermistors and/or medications. The additional lumina do not excessively weaken the intermediate portion of the tubular member 101A because they are provided in the relatively thick section of the tubular wall of the member 101A. It is clear that one of the additional lumina 10 can be omitted or that, if necessary, the tubular member 101A can be provided with more than two additional lumina.

Figure 6:
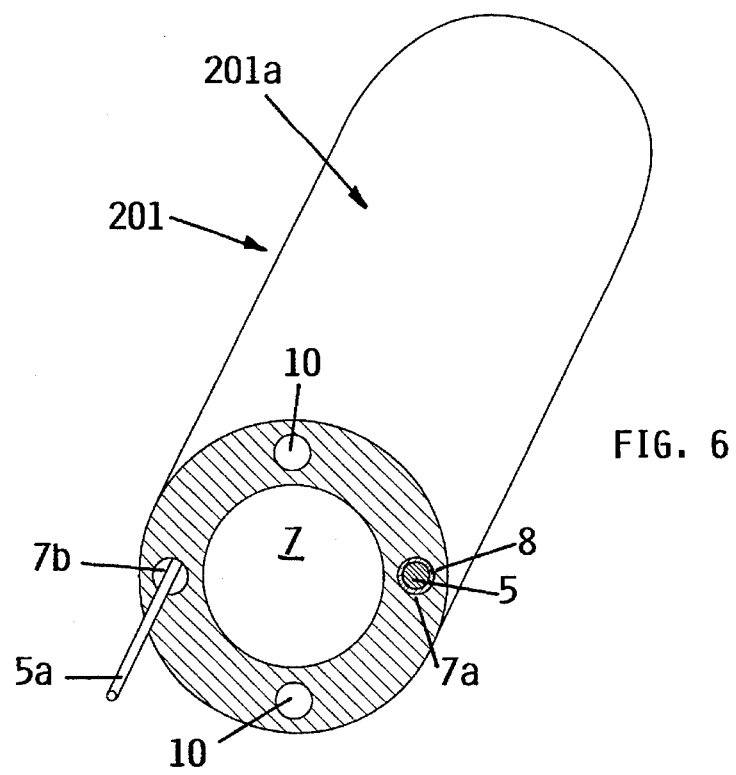
FIG. 6 is a similar greatly enlarged fragmentary partly perspective and partly cross-sectional view of a third catheter.

The catheter 201 of FIG. 6 constitutes a modification of the catheter 101 of FIG. 5. The tubular member 201A of the catheter 201 has a constant or practically constant wall thickness and has a centrally located larger-diameter lumen 7 as well as four at least substantially equidistant smaller-diameter lumina 7a, 7b, 10, 10. The additional lumina 10 are disposed diametrically opposite each other, and the lumen 7a for the flexing element 5 and its guide 8 is disposed at least substantially diametrically opposite the lumen 7b which guides a wire-like or filamentary or strip-shaped stiffening element 5a. The axis of the lumen 7 coincides or can coincide with the center of a circle defined by the outline of the cross-section of the tubular member 201A. The distal end of the element 5a is affixed to the distal end of the intermediate portion of the tubular member 201A and the proximal end of the element 5a is anchored in or at the proximal end of the member 201A. When the flexing element 5 of FIG. 6 is manipulated in a manner as described before with reference to FIGS. 1 to 4, the element 5a opposes flexing of the intermediate portion of the tubular member 201A with the distal end portion of the member 201A. Nevertheless, the element 5a permits that flexing of the intermediate portion of the member 201A which is necessary or desirable to ensure that the intermediate portion can advance along a path which is determined by a blood vessel or another passage in a patient's body.

It is clear that the lumen 7b can also receive a tubular guide 8 or other means for reducing the flexibility of the intermediate portion of the tubular member 201A. Furthermore, the guide 8 of FIG. 6 can be omitted if the element 5a alone or the element 5a in combination with a tubular guide in the lumen 7b suffices to ensure that the intermediate portion of the tubular member 201A can withstand excessive flexing during flexing of the distal end portion of the member 201A.

The thickness of the illustrated element 5 exceeds the thickness of the element 5a. However, it is equally within the purview of the invention to employ a thicker (larger-diameter) element 5a in combination with a smaller-diameter element 5 and to use the sleeve 8 as a guide for the larger-diameter element 5a. It is further within the spirit of the invention to employ an element 5a whose thickness or diameter at least approximates that of the element 5. The illustrated element 5 and/or 5a can be made of metallic wire. Alternatively, the element 5 and/or 5a can be replaced with a strip-shaped element without departing from the spirit of the present invention. Still further, the larger-diameter lumen 7 need not be concentric with the tubular member 201A.

Figure 7:
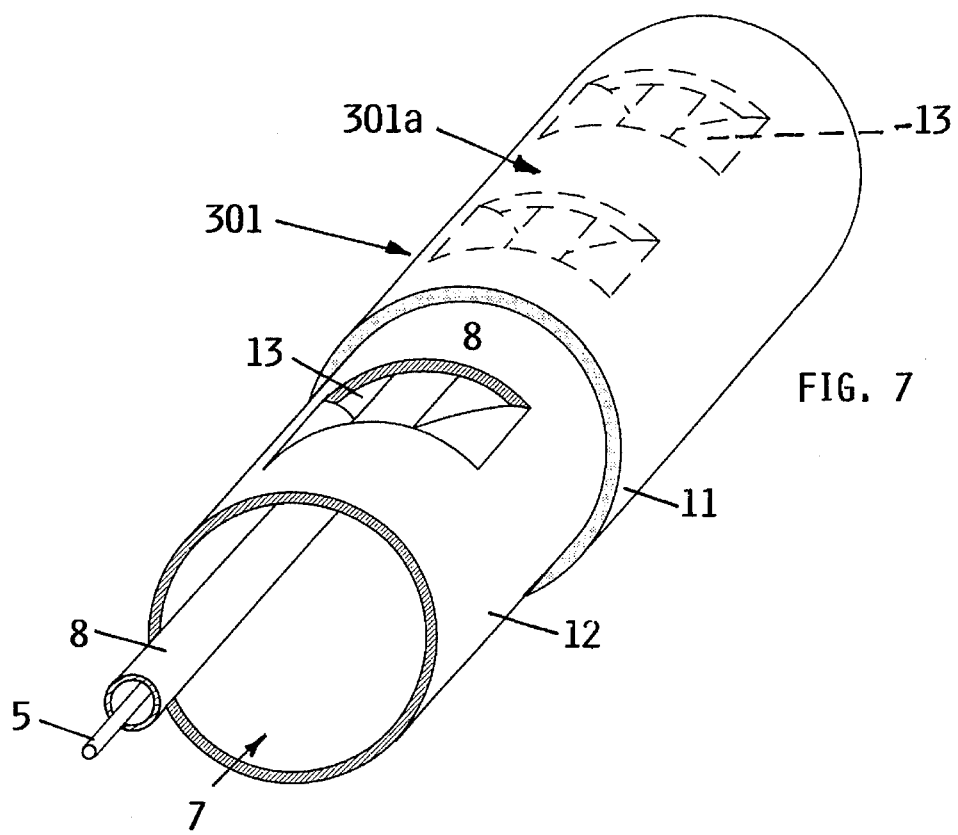
FIG. 7 is a similar greatly enlarged fragmentary partly perspective and partly cross-sectional view of a fourth catheter.

FIG. 7 shows a portion of a catheter 301 wherein the tubular member 301A comprises a flexible outer tube 11 and a flexible inner tube 12 telescoped into the outer tube 11. The tubes 11 and 12 can be made of a suitable synthetic plastic material. The outer tube 11 is devoid or windows, holes or other types of openings in contrast to the inner tube 12 which is provided with windows developing as a result of inwardly bending portions of the tube 12 so as to form means 13 for locating the sleeve-like guide 8 in the coaxial lumen 7 of the tube 12. The locating means 13 resemble or constitute lugs which are of one piece with the inner tube 12 and serve to properly position the guide 8 for the flexing element 5 so that the guide reduces the likelihood of undesirable flexing of the intermediate portion of the tubular member 301A during flexing of the distal end portion of the member 301A. The locating means 13 can constitute simple lugs or fingers which are integral parts of the inner tube 12 and reliably grasp the guide 8 so that the guide 8 and the flexing element 5 therein are properly positioned with reference to the intermediate portion and the distal end portion of the tubular member 301A. The making of the locating means 13 can involve a stamping operation followed by appropriate bending of the resulting lugs or prongs to ensure reliable engagement and retention of the guide 8 relative to the composite tubular member 301A.

If the sleeve-like guide 8 is omitted, the locating prongs or lugs constituting the locating means 13 merely serve to properly position the flexing element 5 relative to the inner tube 12 of the composite tubular member 301A.

The outer tube 11 serves to reliably seal the lumen 7 from the space surrounding the tubular member 301A.

An advantage of the catheter 301 is that the making of the tubular member 301A involves a lower cost because the tubes 11, 12 can be mass-produced at a relatively low cost, especially when compared with the cost of a member (such as 1A) which has an eccentric lumen 7 and one or more smaller lumens (such as the lumen 7a of FIGS. 3 and 4 or the lumens 7a, 10, 10 of FIG. 5) in a relatively thick section of the tubular wall of the respective tubular member.

Figure 8:
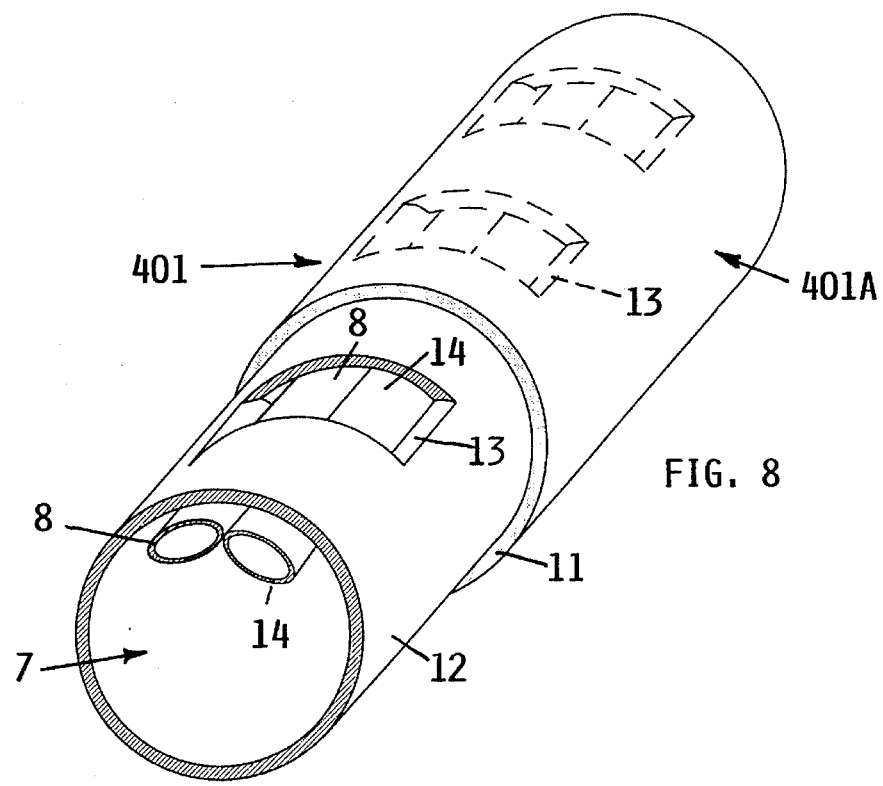
FIG. 8 is a similar greatly enlarged fragmentary partly perspective and partly cross-sectional view of a fifth catheter constituting a modification of the catheter of FIG. 7.

FIG. 8 shows a portion of a catheter 401 comprising an elongated flexible tubular member 401A having two tubes 11, 12 which are telescoped into each other in the same way as described in connection with FIG. 7. The difference between the catheters 301 and 401 is that the locating means 13 of the inner tube 12 of the tubular member 401A serve to properly hold the sleeve-like guide 8 for a flexing element 5 (not shown in FIG. 8) and a second sleeve-like part 14 which is adjacent the guide 8 and serves to enhance the resistance of the intermediate portion of the tubular member 401A to flexing with the distal end portion of such member.

The guide 8 and the sleeve-like part 14 are flattened. An advantage of the flattened guide 8 and of the flattened part 14 is that they take up a small amount of space as seen in the radial direction of the tubular member 401A. This leaves the major part of the centrally located large-diameter lumen 7 of the inner tube 12 for reception of an instrument which is to be introduced into a selected part of a patient's body and/or for admission of one or more medications. The guide 8 of FIG. 8 can receive a flat strip-shaped flexing element which can be made of a metallic or plastic material.

The part 14 can be replaced with a tubular component having a substantially circular cross-sectional outline so that the lumen of the thus modified part 14 can serve for introduction of one or more specific instruments or one or more medications along a path which is at least partially sealed from the lumen 7.

It is further possible to replace the discrete guide 8 and part 14 with a single tubular component which has a plurality of lumina, one for the flexing element and one or more serving the same purpose as the additional lumina 10 shown in FIGS. 5 and 6. Such single tubular component having two or more lumina can be flattened prior to introduction into the lumen 7 of FIG. 8 so that the lumina defined by the thus flattened tubular component can resemble those of the guide 8 and of part 14 in the inner tube 12 of FIG. 8. Flattening of the guide 8 and of the part 14 or of a tubular component replacing the parts 8 and 14 of FIG. 8 can be of particular advantage if the large-diameter lumen 7 is to permit introduction of tongs and/or other relatively bulky instruments or implements into a selected part of a patient's body.

Figures 9, 10:
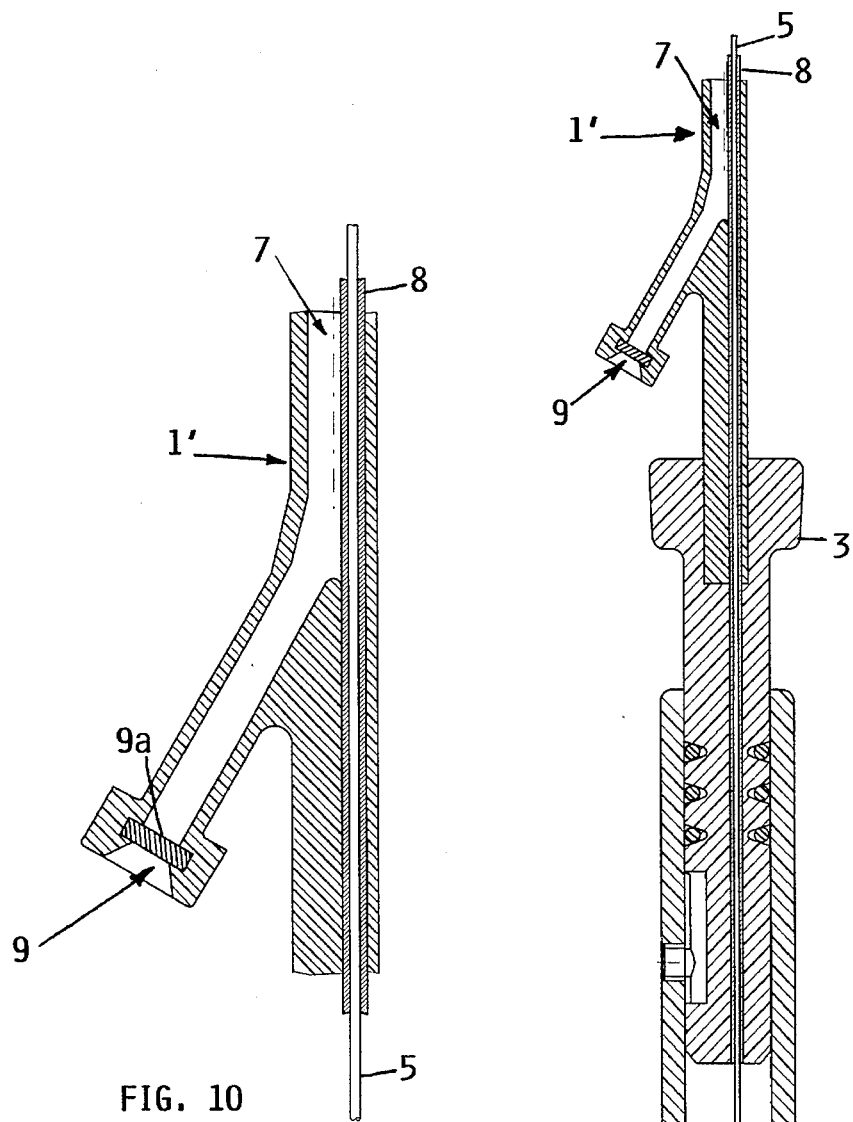
FIG. 9 is an enlarged fragmentary central longitudinal sectional view of the proximal end portion of a catheter which embodies the invention.
FIG. 10 is an enlarged view of a detail in the catheter including the structure of FIG. 9.

FIG. 9 illustrates the proximal end of a catheter 1' which is or can be identical with the catheter 1 of FIGS. 1 to 4 except that the rotary manipulator 2 of FIG. 1 is replaced with the aforediscussed axially movable manipulator 3. The tubular component of the catheter 1' is or can be identical with the tubular component 1A of the catheter 1.

FIG. 10 shows that the inlet 9 can comprise a valve 9a which controls the inflow or outflow of flowable material(s) from the centrally located lumen 7 and/or one or more additional lumina of the tubular member. Moreover, the valve 9a can be removed or moved out of the way to permit insertion of one or more implements or instruments into the lumen 7 and/or one or more additional lumina of the tubular member.

Referring again to FIG. 6, an additional advantage of the stiffening element 5a is that it reduces the likelihood of flexing of the intermediate portion of the tubular member 201A with the distal end portion of the member 201A, but does not prevent or interfere with that flexing of the intermediate portion which is necessary to ensure that the intermediate portion of the member 201A can advance along a path which is defined by an arcuate or otherwise configurated non-linear passage in the body of a patient. Moreover, the resistance of the intermediate portion of the tubular member 201A in the catheter 201 of FIG. 6 to flexing with the distal end portion of the tubular member 201A can be selected practically at will by appropriate selection of the diameter and/or the material and/or another parameter of the stiffening element 5a.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the aforedescribed contribution to the art and, therefore, such adaptations should and are intended to be comprehended within the meaning and range of equivalence of the appended claims.

What is claimed is:

1. A catheter comprising an elongated flexible tubular member including a distal end portion having a first flexibility, an intermediate portion having a lesser second flexibility and at least one longitudinally extending lumen, said tubular member having an at least substantially circular external cross-sectional outline; means for deforming said distal end portion including an elongated flexing element extending within said cross-sectional outline from said distal end portion, through said intermediate portion and to a proximal end portion of said tubular member, said flexing element being a band and being movable relative to and longitudinally of said intermediate portion; and a guide for said element, said guide being disposed within said outline of said tubular member.

2. The catheter of claim 1, wherein said tubular member has a longitudinal axis and at least a major portion of said flexing element is spaced apart from and substantially parallel to said axis.

3. The catheter of claim 1, wherein said tubular member contains a plastic material.

4. The catheter of claim 1, wherein at least said distal end portion and at least a part of said intermediate portion adjacent said distal end portion are devoid of any pronounced external protuberances.

5. The catheter of claim 4, wherein said distal end portion and said part of said intermediate portion have at least substantially smooth external surfaces.

6. The catheter of claim 1, further comprising means for reducing the flexibility of said intermediate portion relative to said distal end portion, said means for reducing being disposed within said outline of said tubular member.

7. The catheter of claim 6, wherein said means for reducing the flexibility of said intermediate portion includes an elongated sleeve surrounding said flexing element.

8. The catheter of claim 7, wherein said sleeve contains a metallic material.

9. The catheter of claim 7, wherein said sleeve contains a plastic material.

10. The catheter of claim 7, wherein said flexing element includes a distal end disposed within said distal end portion of said tubular member and extending beyond said sleeve.

11. The catheter of claim 10, wherein said distal end portion of said tubular member has a free end remote from said intermediate portion and said flexing element has a portion affixed to said free end.

12. The catheter of claim 10, wherein said flexing element includes a portion extending longitudinally within said distal end portion and within said outline of said tubular member.

13. The catheter of claim 7, wherein said sleeve has an inner diameter within the range of between approximately 0.2 and 0.8 mm and an outer diameter within the range of between approximately 0.33 and 1 mm.

14. The catheter of claim 7, wherein said flexing element is received in said sleeve with a radial clearance of between approximately 0.001 and 0.1 mm.

15. The catheter of claim 7, wherein said flexing element is a wire.

16. The catheter of claim 7, wherein said sleeve contains stainless steel.

17. The catheter of claim 1, wherein said intermediate portion of said tubular member includes a first section having a greater wall thickness and being adjacent said flexing element, and a second section of lesser wall thickness remote from said flexing element.

18. The apparatus of claim 17, wherein said sections of said intermediate portion are disposed substantially diametrically opposite each other.

19. The catheter of claim 17, wherein said first section has at least one longitudinally extending second lumen.

20. The apparatus of claim 19, wherein said at least one lumen has a first cross-sectional area and said at least one second lumen has a smaller second cross-sectional area.

21. The catheter of claim 1, wherein said tubular member includes a first tube and a second tube telescoped into said first tube, and further comprising means for reducing the flexibility of said intermediate portion relative to said distal end portion including a sleeve in said second tube, said flexing element extending through said sleeve and one of said tubes having means for locating said sleeve in said second tube.

22. The catheter of claim 21, further comprising a second elongated sleeve in said second tube.

23. The catheter of claim 22, wherein said locating means includes means for locating said second sleeve in said second tube.

24. The catheter of claim 1, further comprising means for reducing the flexibility of said intermediate portion relative to said distal end portion, including an elongated stiffening element disposed in said intermediate portion substantially diametrically opposite said flexing element and having a distal end affixed to said intermediate portion at said distal end portion.

25. The catheter of claim 24, wherein said intermediate portion has a tubular wall of substantially constant thickness, said tubular wall having a longitudinally extending first lumen for said flexing element and a longitudinally extending second lumen for said stiffening element, said first and second lumina being disposed at least substantially diametrically opposite each other.

26. The catheter of claim 25, wherein said tubular member is provided with at least one additional longitudinally extending lumen.

27. The catheter of claim 1, wherein said tubular member is provided with at least one additional longitudinally extending lumen.

28. The catheter of claim 1, wherein said intermediate portion is provided with a second lumen for said flexing element and said guide means includes a portion in said second lumen, said second lumen having an extension for said flexing element in said distal end portion.

29. The catheter of claim 1, wherein said intermediate portion has a second lumen for a first portion of said flexing element, said second lumen having an extension provided in said distal end portion and receiving a second portion of said flexing element, said first portion of said flexing element being disposed at a first distance and said second portion of said flexing element being disposed at a lesser second distance from an external surface of said tubular member.

30. A catheter comprising an elongated flexible tubular member including a distal end portion having a first flexibility, an intermediate portion having a lesser second flexibility and at least one longitudinally extending lumen, said tubular member having an at least substantially circular external cross-sectional outline; means for deforming said distal end portion including an elongated flexing element extending within said cross-sectional outline from said distal end portion, through said intermediate portion and to a proximal end portion of said tubular member, said flexing element being movable relative to and longitudinally of said intermediate portion and said intermediate portion including a first section having a greater wall thickness and being adjacent said flexing element and a second section of lesser wall thickness remote from said flexing element, said first section having at least one longitudinally extending second lumen, said at least one lumen having a first cross-sectional area and said at least one second lumen having a smaller second cross-sectional area; and a guide for said element, said guide being disposed within said outline of said tubular member.

31. A catheter comprising an elongated flexible tubular member incuding a distal end portion having a first flexibility, an intermediate portion having a lesser second flexibility and at least one longitudinally extending lumen, said tubular member having an at least substantially circular external cross-sectional outline; means for deforming said distal end portion including an elongated flexing element extending within said cross-sectional outline from said distal end portion, through said intermediate portion and to a proximal end portion of said tubular member, said flexing element being movable relative to and longitudinally of said intermediate portion and said intermediate portion having a second lumen for a first portion of said flexing element, said second lumen having an extension provided in said distal end portion and receiving a second portion of said flexing element, said first portion of said flexing element being disposed at a first distance and said second portion of said flexing element being disposed at a lesser second distance from an external surface of said tubular member; and a guide for said element, said guide being disposed within said outline of said tubular member.

32. The catheter of claim 1, wherein said flexing element is a wire.

33. The catheter of claim 1, wherein said flexing element is a thread.

34. The catheter of claim 1, wherein said flexing element is a band.

* * * * *